United States Patent [19]

Forster

[11] Patent Number: 5,746,593
[45] Date of Patent: May 5, 1998

[54] ORTHODONTIC DEVICE MADE OF METAL

[75] Inventor: Rolf Forster, Pforzheim, Germany

[73] Assignee: Bernhard Forster GmbH, Pforzheim, Germany

[21] Appl. No.: 725,227

[22] Filed: Sep. 23, 1996

[30] Foreign Application Priority Data

Sep. 21, 1995 [DE] Germany ............ 195 35 095.2

[51] Int. Cl.[6] ............................................. A61C 3/00
[52] U.S. Cl. .......................................... 433/8; 433/9
[58] Field of Search ................. 433/8, 9, 10, 11, 433/12, 13, 14, 15, 16

[56] References Cited

U.S. PATENT DOCUMENTS

| | | | |
|---|---|---|---|
| 2,759,265 | 8/1956 | Johnson | 32/14 |
| 2,769,265 | 11/1956 | Page | 41/26 |
| 4,120,090 | 10/1978 | Kesling | 433/23 |
| 4,304,981 | 12/1981 | Gappa | 219/121 |
| 4,626,209 | 12/1986 | Tsai et al. | 433/9 |
| 5,154,606 | 10/1992 | Wildman | 433/8 |
| 5,232,361 | 8/1993 | Sachdeva et al. | 433/8 |
| 5,238,402 | 8/1993 | Röhlcke et al. | 433/2 |
| 5,252,066 | 10/1993 | Fairhurst | 433/8 |
| 5,288,230 | 2/1994 | Nikutowski et al. | 433/20 |
| 5,326,259 | 7/1994 | Röhlcke et al. | 433/8 |
| 5,358,402 | 10/1994 | Reed et al. | 433/8 |
| 5,613,849 | 3/1997 | Tanaka et al. | 433/9 |

FOREIGN PATENT DOCUMENTS

| | | |
|---|---|---|
| 085484 | 10/1983 | European Pat. Off. . |
| 3868259 | 3/1992 | Germany . |

Primary Examiner—John J. Wilson
Attorney, Agent, or Firm—Martin J. Marcus

[57] ABSTRACT

An orthodontic attachment, in particular a bracket, which is made of metal, consists of a foot section which is made of titanium or of a corrosion-resistant alloy consisting substantially of titanium, for bonding to a tooth, and of a functional section, which is made of stainless steel and which is mounted on the foot section.

16 Claims, 2 Drawing Sheets

ORTHODONTIC DEVICE MADE OF METAL

BACKGROUND OF THE INVENTION (a) Field of the Invention

The invention relates to an orthodontic attachment made of metal.

(b) Description of the Prior Art

An attachment of this type is referred to as a "bracket" in DE-37 27 102 A1. It consists of a foot section, or pad, with which it is bonded to a tooth, and also of a functional section mounted on the foot section. In the case of a bracket, this functional section consists of one or two elements provided with slots and wings. In order to provide the adhesive with a good anchorage base, it is known in the art that the underside of the foot section may be provided with a woven mesh, or that the underside of the foot section may be machined to provide it with a relief structure. Once such an attachment has been bonded to a tooth, using a curable adhesive, the foot section is sealed. If the sealing is defective, or if it becomes defective, saliva can gradually penetrate into the area of the bonded joint. Saliva is an electrolyte and can lead to corrosion, especially pitting corrosion, of the foot section. Since the corrosion occurs at the back of the foot section, it is not discovered until the attachment is removed from the tooth. Unfortunately, the corrosion process causes brown to dark-brown staining of the tooth. Depending on the degree to which the corrosion has progressed, these stains can no longer be removed and they spoil the appearance of the patient's teeth for the rest of the patient's life.

It is also known in the art that these brackets can be made wholly of titanium. Titanium is a material which has found its way into orthodontic usage because of its biocompatibility. When titanium is used, no corrosion is caused by contact with saliva. However, a major disadvantage of titanium is that it is dark grey in colour. Brackets and other orthodontic attachments made of titanium, thus, are not popular with patients because of their unaesthetical appearance.

SUMMARY OF THE INVENTION (a) Aims of the Invention

One object of the present invention is to provide a way in which aesthetically-pleasing orthodontic attachments made of metal can be produced which do not run the risk of causing corrosion stains on teeth.

(b) The present invention provides an orthodontic

An orthodontic attachment or bracket made of metal and consisting of a foot section which is made of titanium or of a corrosion-resistant alloy consisting substantially of titanium, for bonding to a tooth, and of a functional section made of stainless steel which is mounted on said foot section.

(c) Other Features of the Invention

By one feature of this invention the back of the device, where the bonding takes place, consists of titanium or of an alloy consisting substantially of titanium, and the areas which are visible in top view consist of stainless steel.

By another feature of this invention, the foot section is of double-layered construction, having a rear layer which is made of titanium or of an alloy consisting substantially of titanium, and a front layer which is made of stainless steel.

By yet another feature of this invention, the functional section, which is made of steel, is substantially congruent in plan view with the foot section.

By a subsidiary feature of that feature of this invention, the foot section and the functional section, or the two layers of the foot section, are congruent.

By a further subsidiary feature of that feature of this invention, where they are directly joined to the functional section, approximately flush with the edge of the latter, the rear layer or the foot section project a maximum of about 1 mm, preferably about 0.5 mm, beyond the edge of the front layer or of the functional section.

By still another feature of this invention, stainless steel is a low-nickel steel, e.g., containing a maximum of about 1.5 wt % nickel.

By yet a further feature of this invention, the stainless steel is a chromium-manganese steel, e.g., one which bears the material designation 1.4456 (according to DIN).

(d) Generalized Description of the Invention

The invention is suitable principally for brackets, but also for other devices which, like brackets, are attached to the teeth, e.g. buccal tubes.

The combination of a functional section made of stainless steel with a foot section made of titanium, or of a titanium-based alloy, is an economically as well as aesthetically satisfactory solution. The functional section, which is primarily responsible for the aesthetic impression, is made of stainless steel, which does not have the dull grey colour of titanium but instead is shiny in appearance. Consequently, this satisfies the aesthetic requirements, especially when a low-nickel, bright-coloured steel is used. Steel No. 1.4456 (DIN designation) is particularly suitable: it contains about 16 to about 20% manganese, about 16 to about 20% chromium, about 1.8 to about 2.5% magnesium and less than about 0.3% nickel, no more than about 0.1% carbon, no more than about 1% silicon, no more than about 0.05% phosphorus and no more than about 0.05% sulfur, the remainder being iron.

The use of a corrosion-proof titanium material for the foot section, or for the part which is bonded to the tooth, reliably prevents corrosion staining of the teeth. Any corrosion of the functional part made of steel, outside the area of the bond, is acceptable because it does not impair the function of the functional section of the device and cannot harm the teeth. By using steel for the functional section, especially stainless steel No. 1.4456, (as above described) the functional section remains easy to machine, which is not the case when the entire device is made of titanium.

Since the functional section substantially covers the foot section, any parts of the foot section which are not covered over are not important as far as the aesthetic impression is concerned. In addition, it is easy completely to eliminate the aesthetically disadvantageous effect of titanium by selecting external dimensions for the functional section which coincide, in plan view, with those of the foot section, or by giving the foot section a two-layered structure, e.g. a rear layer of titanium and a front layer of steel. In both cases, the titanium material and the steel preferably cover each other congruently, or a small overhang of the titanium part, not more than about 1 mm wide and preferably not more than about 0.5 mm wide, is visible. It would not be so advantageous to allow the steel part to project because it would then be possible for adhesive to penetrate into the unavoidable gap between the steel and the titanium, and that is undesirable.

The titanium and steel parts can be joined together in conventional fashion, especially by soldering, welding or laser welding.

Figure 1:
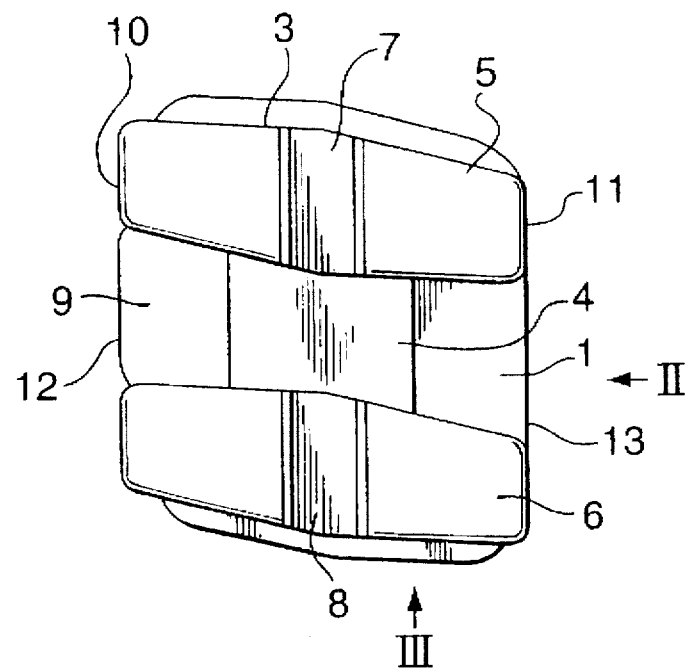
FIG. 1 shows a top view of a bracket according to one embodiment of the invention.
Figure 2:
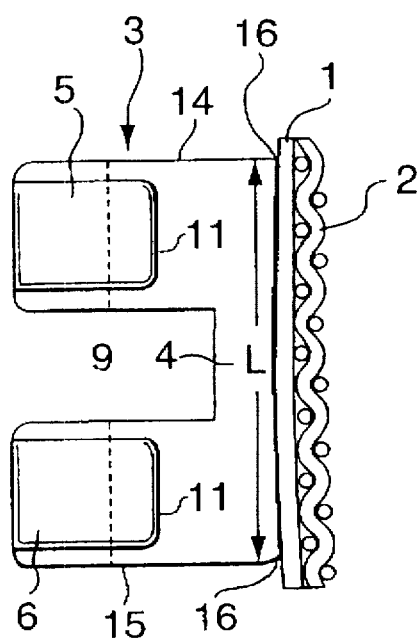
FIG. 2 shows a lateral view of the same bracket shown in FIG. 1, seen in the direction of the arrow II in FIG. 1.
Figure 3:
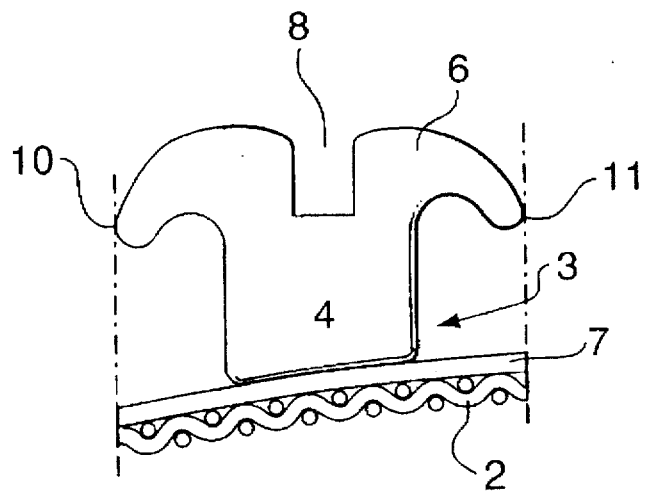
FIG. 3 shows a lateral view of the same bracket shown in FIG. 1, seen in the direction of the arrow III in FIG. 1.

DESCRIPTION OF PREFERRED EMBODIMENT (a) Description of FIGS. 1 to 3

The bracket shown in FIGS. 1 to 3 consists of a foot section or pad 1 having the form of a plate of titanium, to the underside of which is welded a mesh 2 of titanium, the purpose of which is to improve the interlocking with an adhesive with which the pad 1 is bonded to a tooth.

The pad 1 carries a functional section 3 which is made of stainless steel, consisting of a base section 4 which is welded or soldered to the pad. Two double wings 5 and 6, which are subdivided by longitudinal slits 7 and 8 in alignment with each other, as well as by a transverse groove 9, are provided on the base section 4. The dimensions of the wings 5 and 6 are matched to the dimensions of the pad such that, when seen in top view, the ends 10 and 11 of the wings extend as far as, or project slightly beyond, the longitudinal edges 12 or 13. The longitudinal extent L of the base section 4 is selected in such a manner that the pad 1, which is made of titanium, projects slightly, namely by about 0.5 mm, beyond the two narrow ends 14 and 15 of the base section 4. The purpose of this projection is to prevent the adhesive from the joint gap 16 between the pad 1 and the base section 4.

Seen in top view, the functional section 3, which is made from light-coloured, stainless steel, substantially covers the grey titanium pad, thus improving the aesthetic appearance of the bracket.

Figure 4:
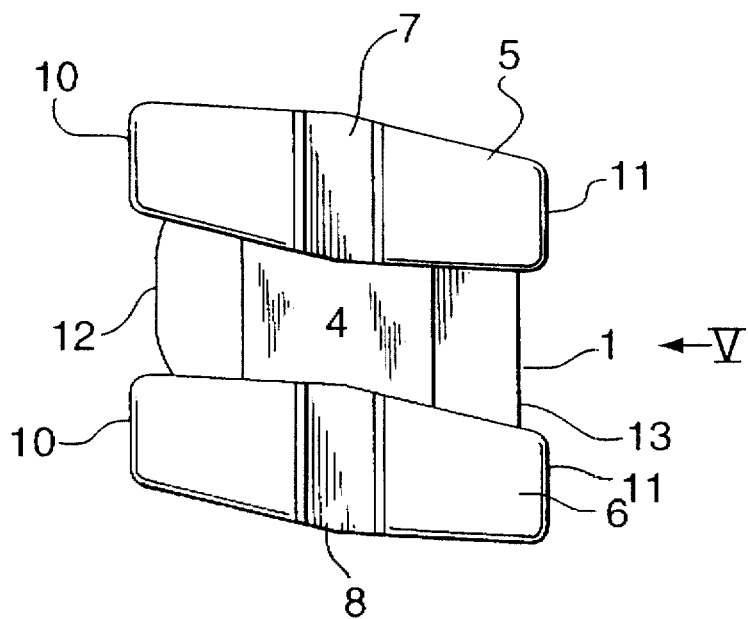
FIG. 4 shows a top view of a bracket according to a second embodiment of the invention.
Figure 5:
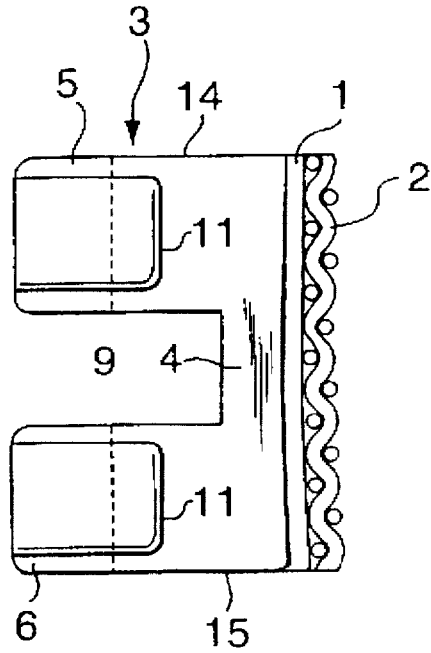
FIG. 5 shows a lateral view of the bracket depicted in FIG. 4, seen in the direction of the arrow V in FIG. 4.

(b) Description of FIGS. 4 and 5

The embodiment illustrated in FIGS. 4 and 5 differs from the first embodiment in that the slight projection of the pad 1 over the narrow ends 14 and 15 of the base section is reduced to zero, thus further reducing the influence which the grey titanium has on the appearance of the pad.

Figure 6:
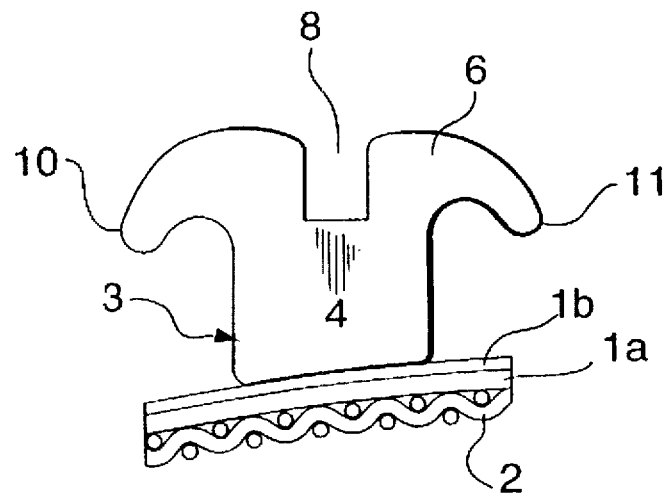
FIG. 6 shows a lateral view of a bracket according to a third embodiment of the invention.

(c) Description of FIG. 6

The embodiment illustrated in FIG. 6 differs from the two preceding embodiments in that the pad itself is of double-layered construction, the lower layer 1a consisting of titanium and the upper layer 1b consisting of stainless steel, and in particular of the same material of which the functional section 3 is made. In all other respects, the structure of this bracket may be the same as that of the first or second embodiment.

In this third embodiment, no titanium is outwardly visible when the bracket is attached to a tooth.

The two layers 1a and 1b may be bonded, soldered or welded together.

CONCLUSION

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and "intended" to be, within the full range of equivalence of the following claims.

I claim:

1. An orthodontic attachment or bracket made of metal and consisting of a foot section which is made of titanium or of a corrosion-resistant alloy consisting substantially of titanium, for bonding to a tooth; and a functional section made of stainless steel which is mounted on said foot section.

2. The attachment according to claim 1, wherein the back of said attachment or bracket where bonding takes place, consists of titanium or of an alloy consisting substantially of titanium; and wherein the areas which are visible in top view consist of stainless steel.

3. An attachment according to claim 2, wherein said foot section is of double-layered construction, having a rear layer which is made of titanium or of an alloy consisting substantially of titanium, and a front layer which is made of stainless steel.

4. The attachment according to claim 3, wherein said foot section and said functional section, or said two layers of said foot section, are congruent.

5. The attachment according to claim 3, wherein, where they are directly joined to the functional section, approximately flush with the edge of the latter, said rear layer or said foot section projects a maximum of 1 mm, beyond the edge of said front layer or of said functional section.

6. The attachment according to claim 5, wherein, said rear layer or said foot section projects a maximum of 0.5 mm, beyond the edge of said front layer or of said functional section.

7. The attachment according to claim 2, wherein said functional section, which is made of steel, is substantially congruent in plan view with said foot section.

8. An attachment according to claim 1, wherein said foot section is of double-layered construction, having a rear layer which is made of titanium or of an alloy consisting substantially of titanium, and a front layer which is made of stainless steel.

9. The attachment according to claim 8, wherein said foot section and said functional section, or said two layers of said foot section, are congruent.

10. The attachment according to claim 8, wherein, where they are directly joined to the functional section, approximately flush with the edge of the latter, said rear layer or said foot section projects a maximum of 1 mm, beyond the edge of the front layer or of the functional section.

11. The attachment according to claim 10, wherein said rear layer or said foot section projects a maximum of 0.5 mm, beyond the edge of said front layer or of said functional section.

12. The attachment according to claim 1, wherein said functional section, which is made of steel, is substantially congruent in plan view with said foot section.

13. The attachment according to claim 1, wherein stainless steel is a low-nickel steel.

14. The attachment according to claim 13, wherein said stainless steel contains a maximum of 1.5 wt. % nickel.

15. An attachment according to claim 1, wherein said stainless steel is a chromium-manganese steel.

16. The attachment according to claim 15, wherein stainless steel bears the material designation 1.4456 (according to DIN).

* * * * *